(12) United States Patent
Lesser et al.

(10) Patent No.: US 10,322,284 B2
(45) Date of Patent: Jun. 18, 2019

(54) METHOD FOR TREATING NAUSEA AND VOMITING BY VAGUS NERVE STIMULATION WITH SELECTABLE STIMULATION MODES

(75) Inventors: Ronald P. Lesser, Baltimore, MD (US); Robert S. Webber, Ellicott City, MD (US)

(73) Assignee: The John Hopkins University, Baltimore, MD (US)

( * ) Notice: Subject to any disclaimer, the term of this patent is extended or adjusted under 35 U.S.C. 154(b) by 2258 days.

(21) Appl. No.: 10/565,262

(22) PCT Filed: Jul. 19, 2004

(86) PCT No.: PCT/US2004/023146
§ 371 (c)(1),
(2), (4) Date: Apr. 2, 2008

(87) PCT Pub. No.: WO2005/007120
PCT Pub. Date: Jan. 27, 2005

(65) Prior Publication Data
US 2008/0208266 A1 Aug. 28, 2008

Related U.S. Application Data

(60) Provisional application No. 60/488,525, filed on Jul. 18, 2003.

(51) Int. Cl.
*A61N 1/36* (2006.01)
*A61N 2/00* (2006.01)

(52) U.S. Cl.
CPC ........ *A61N 1/36114* (2013.01); *A61N 1/3606* (2013.01); *A61N 1/36014* (2013.01); *A61N 1/36053* (2013.01); *A61N 2/006* (2013.01)

(58) Field of Classification Search
None
See application file for complete search history.

(56) References Cited

U.S. PATENT DOCUMENTS 4,865,048 A * 9/1989 Eckerson .................. 607/45
5,231,988 A * 8/1993 Wernicke ........... A61N 1/36053
600/319

(Continued)

OTHER PUBLICATIONS

International Preliminary Report on Patentability, dated Jan. 23, 2006 for PCT Application No. PCT/US2004/023146.

*Primary Examiner* — Kennedy Schaetzle
(74) *Attorney, Agent, or Firm* — Mintz Levin Cohn Ferris Glovsky and Popeo, P.C.; Peter F. Corless

(57) ABSTRACT

A system and method for treating nausea and vomiting are provided, including one or more electrodes (10, 12) applied on or under the skin, the electrodes being connected to an external current source (34). The electrodes can be implanted under the skin and connect to internal stimulator electronics (22), which can form a magnetic inductive link to the external current source (34). Alternatively, the electrodes can be placed on the skin and directly linked by wires to the external current source. As a further alternative, the vagus nerve can be directly stimulated in the neck, or the esophagus, stomach, duodenum, or intestines can be directly stimulated by magnetic stimulation. The electrodes can stimulate the vagus nerve in the neck to reduce nausea and vomiting, or can be arranged near the chest or abdomen, so as to stimulate the esophagus, stomach, duodenum or intestines. Because the current source is provided outside the body, it is not necessary to implant batteries or another power supply in the body.

12 Claims, 5 Drawing Sheets

(56) References Cited

U.S. PATENT DOCUMENTS

| | | |
|---|---|---|
| 5,514,175 A | 5/1996 | Kim et al. |
| 6,571,127 B1 | 5/2003 | Ben-Haim et al. |
| 6,754,536 B2 | 6/2004 | Swoyer et al. |
| 6,853,862 B1 * | 2/2005 | Marchal et al. ................. 607/40 |
| 7,010,351 B2 * | 3/2006 | Firlik .................... A61N 1/0531 607/2 |
| 2004/0059393 A1 | 3/2004 | Policker et al. |
| 2004/0064166 A1 * | 4/2004 | Thompson ......... A61N 1/37252 607/60 |
| 2004/0158298 A1 * | 8/2004 | Gliner ................. A61N 1/0531 607/48 |

\* cited by examiner

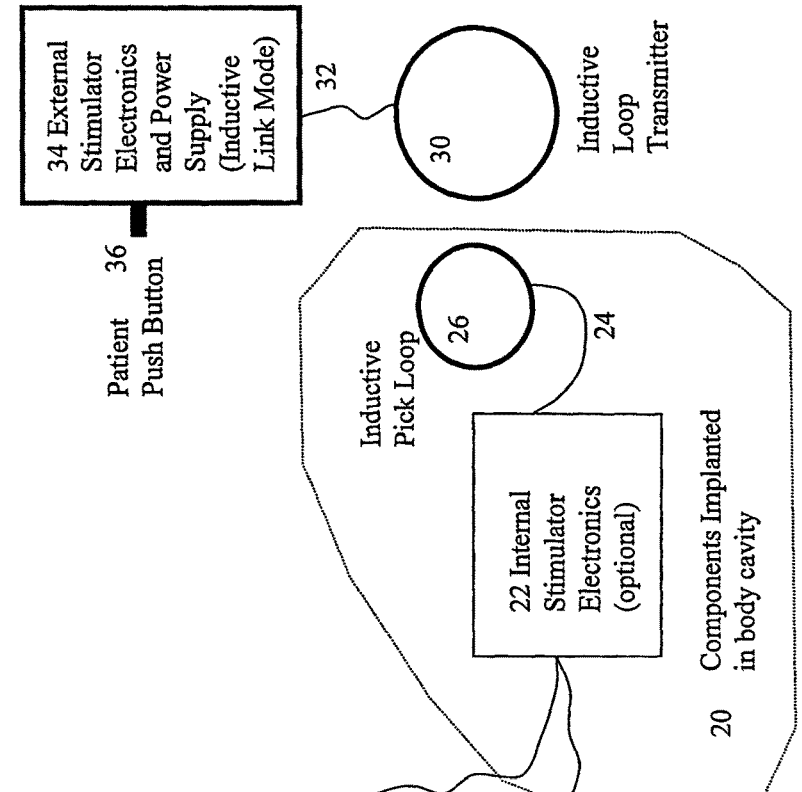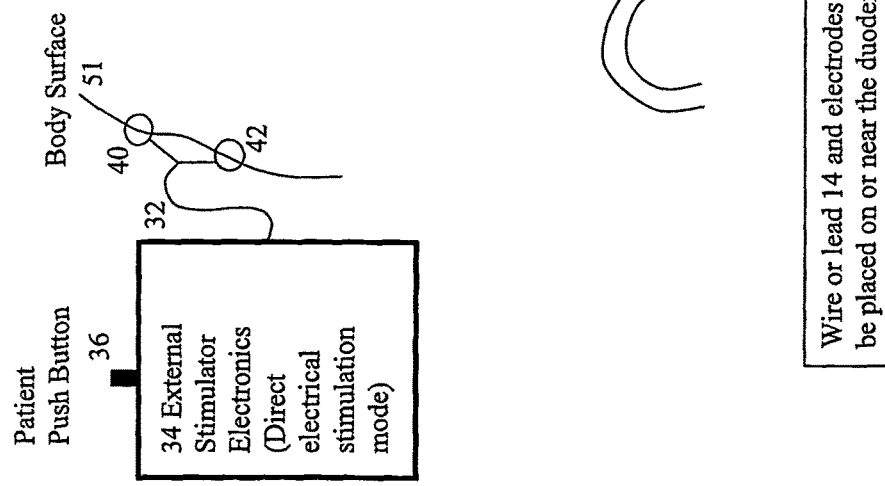

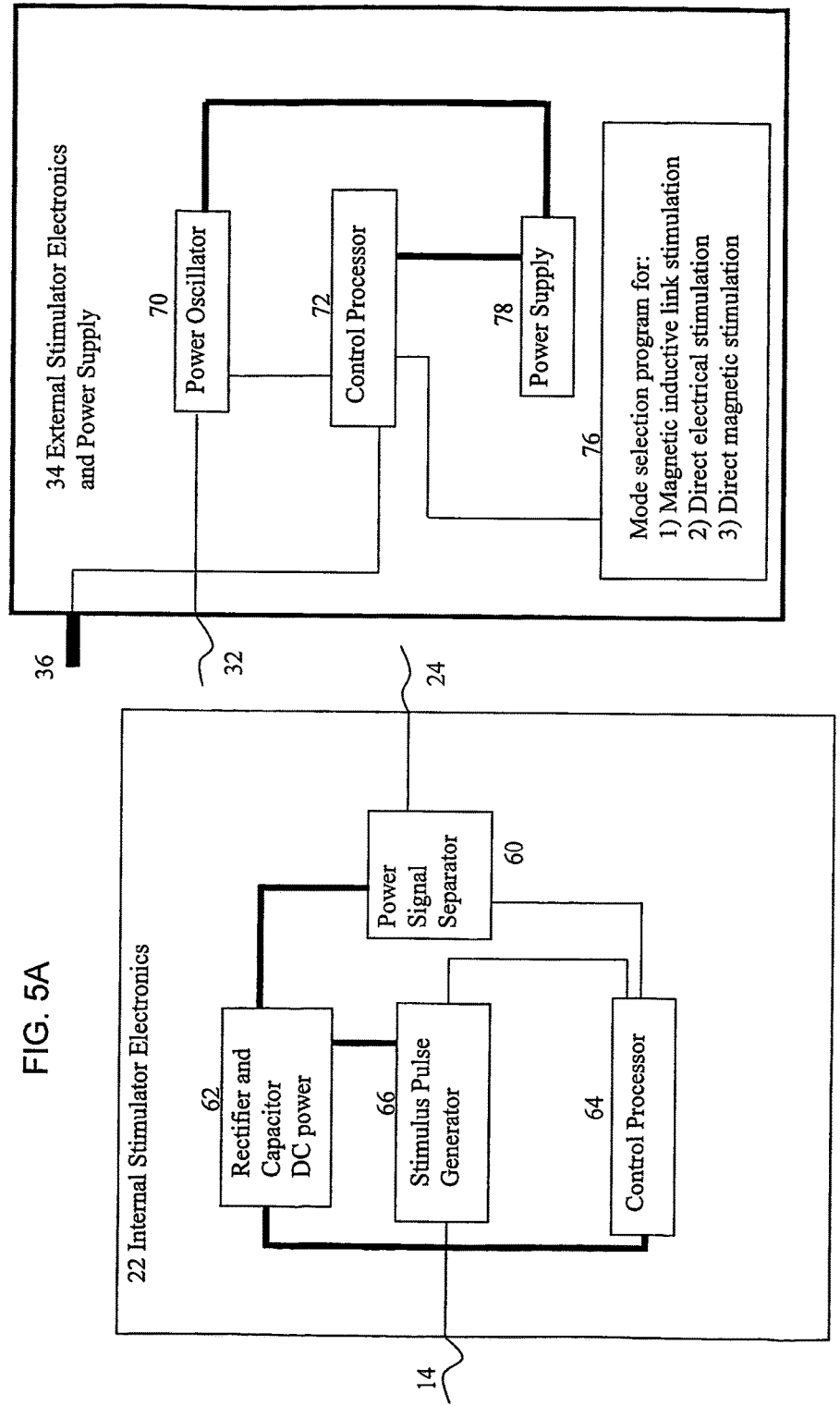

METHOD FOR TREATING NAUSEA AND VOMITING BY VAGUS NERVE STIMULATION WITH SELECTABLE STIMULATION MODES

CROSS-REFERENCE TO RELATED APPLICATION

This application claims the benefit of U.S. Provisional Application Ser. No. 60/488,525 filed on Jul. 18, 2003, the teachings of which are incorporated herein by reference.

FIELD OF INVENTION

The present invention relates to systems and methods for treating nausea and vomiting by application of electrical signals to a selected cranial nerve, nerve branch, or nerve bundle, and more particularly to techniques for treating patients for nausea and vomiting by stimulating the vagus nerve in the patient's neck, stomach, esophagus, duodenum, or intestines.

BACKGROUND OF THE INVENTION

Nausea and vomiting are significant problems during pregnancy, affecting about 70 to 80% of women during early pregnancy, and about 20% of women throughout pregnancy. In a smaller number of women, about 0.3 to 2%, the symptoms are severe enough to cause significant dehydration, disturbed electrolyte balance, weight loss, and ketosis, which can lead to a condition known as hyperemesis gravidarum. In certain cases, hospital admission may be necessary.

Medications for emesis are available, but none are universally effective. Moreover, medications carry a risk of fetal malformations and their use is discouraged (see C. Broussard et al., "Treating gastro-esophageal reflux disease during pregnancy and lactation: What are the safest therapy options?" *Drug Saf.* 1998, 19: 325-37). Although fluids and electrolytes can be replenished, and general nutrition promoted in a pregnant woman, nausea and vomiting still cause considerable discomfort, and no ideal treatment is available. It is well known that the gastrointestinal tract is innervated by the vagus nerve, and it has been shown conceptually that stimulation of vagal fibers can suppress experimental vomiting. See Zabara et al., "Neuroinhibition in the regulation of emesis," *Space Life Sci.,* 1972, 3: 282-92; Zabara, "Neuroinhibition of xylazine induced emesis," *Pharamacol. Toxicol.* 1988, 63: 70-74.

Patients often suffer from nausea and vomiting as a result of chemotherapy treatments. For example, chemotherapy treatments for diseases such as cancer, severe forms of connective tissue diseases or inflammatory diseases of the body, or inflammatory or autoimmune disorders of the peripheral or central nervous system can require use of agents that produce nausea, vomiting, or both. Examples of connective tissue diseases or inflammatory diseases of the body include disorders such as lupus erythematosus, rheumatoid arthritis, scleroderma, dermatomyositis, and ulcerative colitis. Examples of inflammatory or autoimmune disorders of the peripheral nerves or central nervous system include disorders such as chronic inflammatory demyelinating polyneuropathy, multiple sclerosis, neurosarcoidosis, central nervous system lupus, central nervous system vasculitis, and monoclonal gammopathy. Finally, some patients experience severe motion sickness. Moreover, the disorders listed above can themselves cause nausea or vomiting. Although medications are available for treating these conditions, none are universally effective.

U.S. Pat. No. 4,981,146 to Bertolucci discloses a nausea control device for electrically stimulating the wrist in the region of the median nerve, at the P6 acupuncture point. However, this treatment for nausea is not universally or completely effective.

Direct vagus nerve stimulation has been used clinically for the treatment of intractable seizures of partial onset (see, e.g., U.S. Pat. Nos. 5,025,807; 4,867,164; and 4,702,254, all to Zabara). According to these Zabara patents, a neurocybernetic prosthesis is placed surgically within the neck, in direct proximity to the vagus nerve. Direct stimulation of the vagus nerve primarily causes localized effects in the area of stimulation. Common symptoms include hoarseness, throat pain, coughing, and dyspnea, paresthesias, and muscle pain, occurring at the time of stimulation. Importantly, there is no evidence to suggest that vagus nerve stimulation causes effects elsewhere in the body or causes birth defects (see E. Ben-Menachem et al., "Gestational outcomes in patients with epilepsy receiving vagus nerve stimulation," *Epilepsia* 1998, 39 (suppl 6): 180).

Vagus nerve stimulation has been envisioned as a treatment for disorders other than epilepsy, including psychiatric disorders. Stimulation of other cranial nerves has been envisioned for treating a variety of neurological disorders including voluntary and involuntary disorders; migraine; epileptic seizures; motor disorders; Parkinson's disease; cerebral palsy; spasticity; chronic nervous illnesses and involuntary movement disorders; pancreatic endocrine disorders including diabetes and hypoglycemia; dementia including cortical, subcortical, multi-infarct, Alzheimer's disease and Pick's disease; sleep disorders including central sleep apnea, insomnia and hypersomnia; eating disorders including anorexia nervosa, bulimia and compulsive overeating; and neuropsychiatric disorders including schizophrenia, depression and borderline personality disorder (see U.S. Pat. No. 5,299,569 to Wernicke et al. and U.S. Pat. No. 5,540,734 to Zabara).

Vagus nerve stimulation also has been envisioned for treating heart disorders (see U.S. Pat. No. 5,700,282 to Zabara), hypertension (see U.S. Pat. No. 5,707,400 to Terry, Jr. et al.), endocrine disorders such as diabetes and hypoglycemia (see U.S. Pat. No. 5,231,988 to Wernicke et al.). It also has been envisioned to treat gastric motility disorders such as duodenal ulcers, irritable colon, diverticulosis, and dumping syndrome (see U.S. Pat. No. 5,540,730 to Terry, Jr. et al.). However, the '730 patent does not describe a method or system for treating nausea or vomiting by stimulating the vagus nerve on a patient's neck, and further does not describe stimulator electronics with a power supply arranged outside the patient's body. In the '730 patent, the stimulus generator is implanted in the patient's body, such as below the skin covering the abdomen. An implanted battery supply or other power supply is undesirable for many patients, such as pregnant women, where the source of nausea or vomiting may be transitory.

It would be desirable to provide improved methods and systems for treating nausea and vomiting. It would also be desirable to locate a current source for such methods and systems outside the body, for patients who do not need or desire an implanted power supply or battery operated device. Such methods and systems should overcome the deficiencies of the presently available methods and systems.

SUMMARY OF THE INVENTION

A method for treating nausea and/or vomiting according to the present invention includes a step of applying electrical current from an external current source to a vagus nerve of a patient to reduce nausea and/or vomiting. The external current source is positioned outside the body, thereby eliminating the need to implant batteries or another power source.

A system and method for treating nausea and vomiting according to the present invention includes one or more electrodes applied on or under the skin, the electrodes being connected to an external current source. The electrodes can be implanted beneath the skin, in proximity to the vagus nerve, and connected to internal stimulator electronics, which can form a magnetic inductive link to the external current source. Alternatively, the electrodes can be placed on the skin and directly linked by wires to the external current source. As used herein, the terms "electrode" and "electrodes" refer to both the actual electrode(s) and the lead(s) or wire(s) attached to each electrode. The electrodes can stimulate the vagus nerve in the neck to reduce nausea and vomiting, or can be arranged near the esophagus, stomach, duodenum, or intestines, stimulating those organs or their nerves.

The current source is provided externally, i.e., outside the body, as compared to prior art devices which utilize an implanted power supply, such as the stimulus generator disclosed in U.S. Pat. No. 5,154,172 to Terry, Jr. et al. Because the current source is provided outside the body, it is not necessary to implant batteries or another type of power supply in the body. The external power supply utilized in the present invention is particularly beneficial for persons who do not need or desire a battery pack or other power supply implanted in the body cavity. For example, pregnant women may be treated for nausea and vomiting according to the present invention, but since nausea or vomiting may not occur after pregnancy, it is desirable to minimize or eliminate implanted components. Therefore, the power supply and/or other components of the system can be provided externally. The terms "power supply" and "current source" are used interchangeably herein.

The present invention also can be used to treat patients who suffer from nausea and vomiting as a result of chemotherapy treatments. For example, chemotherapy treatments for diseases such as cancer, severe forms of connective tissue diseases or inflammatory diseases of the body, or inflammatory or autoimmune disorders of the peripheral or central nervous system can require use of agents that produce nausea, vomiting, or both. Finally, some patients experience severe motion sickness.

Current from outside the body can be delivered to an implanted device (e.g., an inductive pickup loop) by magnetic induction. The magnetic inductive link is a conventional magnetic inductive link suitable for signal transmission and/or power transmission across short distances, which can transmit signals and power from an external coil to an implanted device, according to the present invention. The magnetic inductive link includes two coils of wire separated by a short distance, where the external coil is positioned outside the patient, and the implanted coil preferably is implanted just below the surface of the skin. Therefore, when a varying current is passed through the external coil, a varying magnetic field is created, which induces electrical currents in the implanted coil.

Stimulation of the vagus nerve can be performed as a single pulse, or as a train of pulses. The electrical pulses can be applied manually by the patient or attending physician, or automatically according to a programmed sequence. Further, the electrical pulses can be applied continuously, periodically, or intermittently to the vagus nerve. Various characteristics of the pulses can be controlled, including pulse amplitude (measured in amperes or joules), pulse duration, pulse train duration, and frequency of pulse or pulse train repetition. The external current source can be a conventional alternating current (AC) power supply. Alternatively, the current source can supply current from a direct current (DC) power supply, or one or more batteries.

According to one embodiment of the present invention, electrodes are placed beneath the skin, with no direct "wired" connection to the outside. These electrodes can be configured and arranged directly under the skin, or deeper, such as below the sternocleidomastoid muscle, so as to be closer to the vagus nerve. Stimulation preferably is delivered to the electrodes and their associated electronics by means of induction through the skin.

According to another embodiment of the present invention, the stimulator electrodes are connected directly to an implanted inductive link coil, and all of the electronics are external. In this case, the timing, current, and pulse shape are entirely controlled by the corresponding driving current in the external coil of the magnetic inductive link.

According to a further embodiment of the present invention, stimulator electrodes can be held in place on the skin of the neck, abdomen, or near the vagus nerve fibers in the vicinity of the esophagus, stomach, duodenum or intestines.

According to yet a further embodiment, stimulation occurs solely by external magnetic stimulation.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIGS. 4A and 4B are schematic views for driving current according to the first and second embodiments, respectively, whereby electrodes are positioned on or near the stomach and esophagus; and FIGS. 5A and 5B are schematic diagrams of the internal and external stimulator electronics, respectively.

DEFINITIONS

Figure 1:
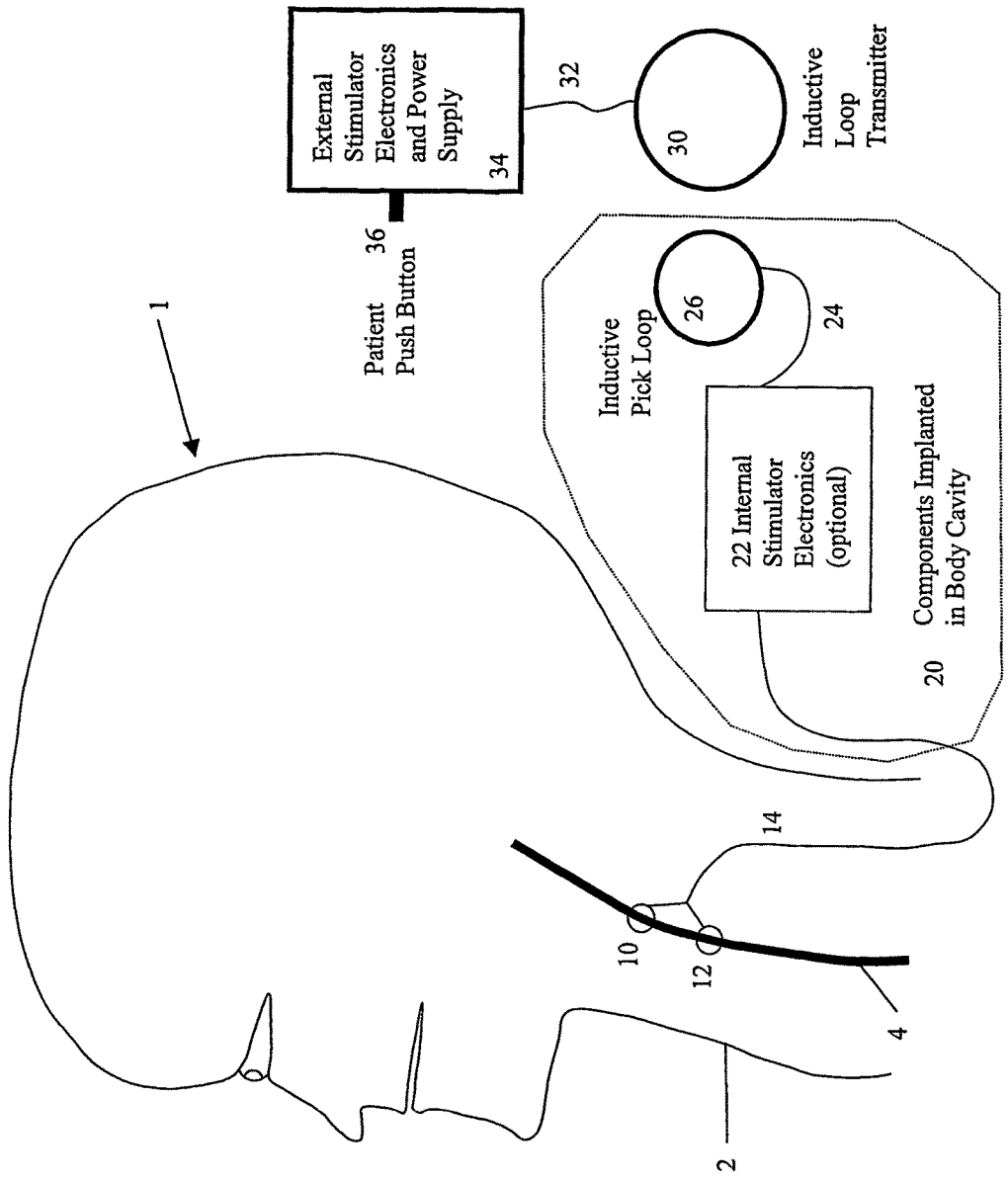
FIG. 1 is a schematic view illustrating a system and method for stimulating the vagus nerve, which utilizes magnetic induction, and optionally internal stimulator electronics, for driving current to stimulate one or more electrodes, according to the present invention.

The instant invention is most clearly understood with reference to the following definitions:

As used in the specification and claims, the singular form "a", "an" and "the" include plural references unless the context clearly dictates otherwise.

As used herein, a "patient" is a vertebrate, preferably a mammal, more preferably a human. Mammals include, but are not limited to, murines, simians, humans, farm animals, sport animals, and pets.

DETAILED DESCRIPTION OF THE INVENTION

The present invention is directed to techniques for treating nausea and/or vomiting by stimulation of the vagus nerve, preferably by attaching electrodes on or under the skin of the patient's neck, near the vagus nerve fibers in the neck. Vagus nerve stimulation also can be performed on or under the skin of the chest or abdomen, such near the esophagus, or in the vicinity of the stomach, duodenum, or intestines. According to the present invention, the electrodes are connected to a power source provided outside the body, as distinguished from an implanted power source.

The vagus nerve is a mixed nerve, and a primary function of this nerve is to innervate the heart, lungs, and gastrointestinal system. The right vagus nerve innervates the atria of the heart, the left vagus nerve innervates the ventricles. The vagus nerve in the neck travels beneath the sternocleidomastoid muscle, and is about an inch or more below the skin surface. Fibers of the vagus nerve that connect to the ventricles are less plentiful, so stimulation of the left vagus nerve is less likely to disrupt cardiac rhythm. Fibers from the left vagus nerve travel via the ventral surface of the esophagus, through the diaphragm, and then primarily to the anterior surface of the stomach. The intestines are innervated by nerves that accompany their arterial blood supply.

Stimulation of the vagus nerve can be performed as a single pulse, or as a train of pulses. The electrical pulses can be applied manually by the patient or attending physician, or automatically according to a programmed sequence. Further, the electrical pulses can be applied continuously, periodically, or intermittently to the vagus nerve. Various characteristics of the pulses can be controlled, including pulse amplitude (measured in amperes or joules), pulse duration, pulse train duration, and frequency of pulse or pulse train repetition.

Stimulation can be accomplished by placing the stimulating electrodes directly on the neck, or by attaching electrodes to the neck, either on or under the skin. It is well known that electrodes can be attached easily in a number of ways. For example, each electrode can be attached to the neck using an adhesive or coating material, such as paste or collusion, or the electrodes can be shaped so that they can be introduced through a needle or catheter and placed under the skin. In a preferred embodiment, the electrodes are placed on the left side of the neck, over the vagus nerve, so as to stimulate the left vagus nerve. The present invention also encompasses attaching or placing electrodes on the right side of the neck to stimulate the right vagus nerve, or on both sides of the neck to stimulate the left and right vagus nerves. According to the present invention, electrodes can be provided on or under the skin of the chest or abdomen, near the patient's esophagus, stomach, duodenum or intestines, thereby stimulating those organs or their nerves.

According to one embodiment of the present invention, electrodes are placed under the skin, with no direct "wired" connection to the outside. These electrodes can be configured and arranged directly under the skin, or deeper, such as below the sternocleidomastoid muscle, so as to be closer to the vagus nerve. Stimulation preferably is delivered to the electrodes and their associated electronics by means of induction through the skin.

According to another embodiment of the present invention, stimulator electrodes are held in place on the skin of the neck, abdomen, or near the vagus nerve fibers in the vicinity of the stomach or esophagus.

According to the present invention, a current source is located externally, i.e., outside the body, as compared to prior art devices which utilize an implantable power supply. In the present invention, the current source is provided outside the body, thereby avoiding unnecessary surgery to implant the current source or power supply, especially for persons who do not need or desire a battery pack or other power supply implanted in the body cavity. For example, pregnant women may be treated for nausea and vomiting according to the present invention, but since nausea or vomiting may not occur after pregnancy, it is desirable to minimize or eliminate implanted components. Therefore, the power supply and/or other components of the system can be provided externally. The terms "power supply" and "current source" are used interchangeably herein.

According to the present invention, the current source can be connected directly to the electrodes by means of wires, or alternatively, current is delivered through the skin to implanted electrodes and their associated electronics by means of induction. The electrodes can be in a variety of shapes including discs and wires. Electrodes can be reusable or disposable according to the invention.

Stimulation of the vagus nerve can be accomplished by magnetic stimulation. The magnetic stimulation can be focused, so that the effects of stimulation are localized to a specific region for which activation is desired. Since the nerve can be positioned differently in different people, two- or three-dimensional imaging (i.e. magnetic resonance imaging or computerized tomography) can be used to precisely locate the target nerve region and target this region with respect to specific locations on the skin surface. According to the present invention, implantable devices can be introduced percutaneously through very small openings, with the final destination of the devices determined by using methods such as two and three-dimensional imaging and fiber optic visualization.

FIG. 1 depicts a first preferred embodiment of the present invention, in which one or more electrodes are implanted under the skin of a patient 1. Preferably, at least two electrodes 10 and 12 are arranged under the skin of a patient's neck 2 in the vicinity of the vagus nerve 4. The electrodes 10 and 12 can be placed under the skin proximate the vagus nerve, or below the sternocleidomastoid muscle, so as to be closer to the vagus nerve. Preferably, the electrodes 10 and 12 are placed on or under the skin on the left side of the neck 2 over the vagus nerve, so as to stimulate the left vagus nerve. Alternatively, electrodes can be placed on or under the skin on the right side of the neck to stimulate the right vagus nerve, or on both sides of the neck to stimulate both the left and right vagus nerves. One or more leads (usually wires) 14 connect the electrodes 10 and 12 to an implanted electronics package ("internal stimulator electronics") 22.

The internal stimulator electronics 22 preferably include conventional electronics circuitry capable of transmitting pulses over the wire 14 to the electrodes 10 and 12. The internal stimulator electronics 22 are connected by one or more second wires 24 to an inductive pickup coil ("inductive pick loop") 26. The internal stimulator electronics 22, wire 24, and inductive pickup coil 26 constitute the components 20 that are implanted in the body cavity of the patient 1. The implanted components 20 can be surgically implanted in any suitable location of the body cavity away from the patient's neck. For example, one suitable location for implantation is a pocket formed just below the skin of the abdomen.

Optionally, the internal stimulator electronics 22 can be omitted, and instead, the electronics would be entirely external. In such a case, the timing, current, pulse shape, and other parameters are entirely controlled by external stimulator electronics.

The internal stimulator electronics 22 derive power from an external inductive loop transmitter 30 that can be placed over the implanted pickup coil 26. Control information for controlling the train of pulses output by the internal stimulator electronics 22 is transmitted by a magnetic inductive link formed by the inductive loop transmitter 30 and the inductive pickup coil 26. The inductive loop transmitter 30 is linked by one or more cables 32 to external stimulator electronics and power supply 34, which preferably include a conventional alternating current (AC) power supply and control mechanism. Alternatively, the power supply can be a direct current (DC) power supply, or can include one or more batteries.

The external stimulator electronics and power supply 34 are capable of delivering periodic or continuous stimulation at the desired level, either under program control or on demand by pressing a button 36. For example, the electronics and power supply 34 can be programmed to deliver pulses periodically, or be turned on and off at designated times. Various characteristics of the pulses can be controlled, including pulse amplitude (measured in amperes or joules), pulse duration, pulse train duration, and frequency of pulse or pulse train repetition. The patient push button 36 can be included with the external stimulator electronics and power supply 34, or provided as a separate component, the button 36 being provided to enable the patient or attending physician to actuate the electronics and power supply 34 and deliver one or more electric pulses to the electrodes 10 and 12 by pressing the button 36.

In use, the components 20 are implanted in a suitable body cavity, and electrodes 10 and 12 are placed under the skin near the vagus nerve. The patient or attending physician turns on the external stimulator electronics and power supply 34 and enters suitable control parameters, and then moves the inductive loop transmitter 30 in close proximity to the inductive pickup loop 26, thereby forming the magnetic inductive link and transferring power to the inductive pickup loop 26 and the internal stimulator electronics 22. Thus, one or more pulses are delivered to the electrodes 10 and 12 as programmed into the external stimulator electronics and power supply 34. Power can also be delivered to the electrodes 10 and 12 upon pressing the button 36.

Figure 2:
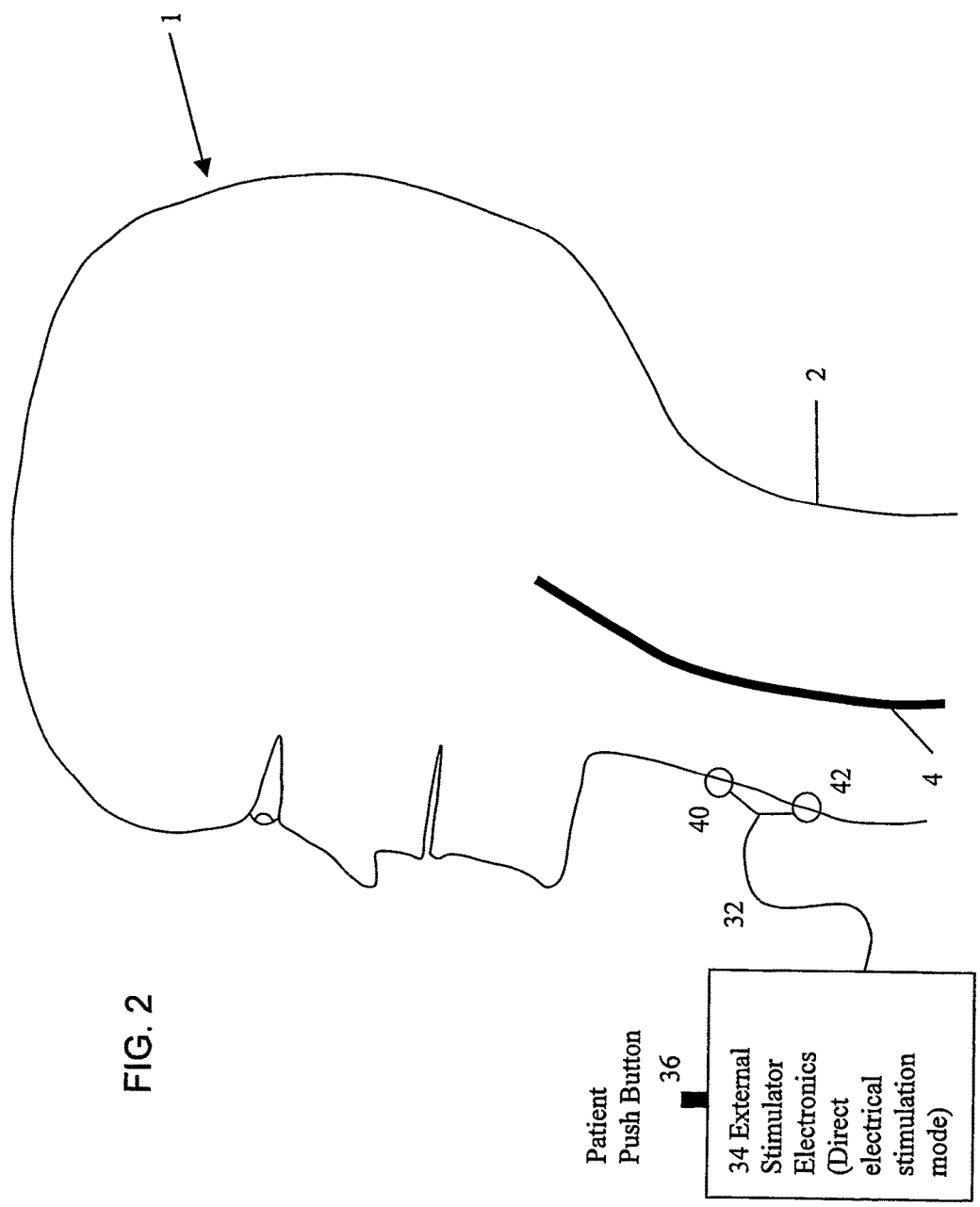
FIG. 2 is a schematic view of an alternate system and method for stimulating the vagus nerve, including external stimulator electronics which are driven in a direct electrical stimulation mode.

FIG. 2 depicts a second preferred embodiment of the present invention, in which one or more electrodes are placed on the skin surface of the patient 1. Preferably, at least two electrodes 40 and 42 are arranged on the skin of the patient's neck 2 in the vicinity of the vagus nerve 4. As in the first preferred embodiment, the electrodes 40 and 42 preferably are placed on or under the skin of the left side of the neck 2 over the vagus nerve, so as to stimulate the left vagus nerve. Alternatively, electrodes can be placed on or under the skin of the right side of the neck to stimulate the right vagus nerve, or on both sides of the neck to stimulate both the left and right vagus nerves.

The electrodes 40 and 42 are connected by one or more wires or cables 32 to external stimulator electronics and power supply 34. A patient push button 36 can be pressed to provide on demand stimulation, as described above. The external stimulator electronics 34 can be programmed to deliver periodic or continuous stimulation at the desired level, either under program control or on demand. The external stimulator electronics 34 can be powered by a direct current power supply, an alternating current power supply, one or more batteries, or by magnetic induction. In other words, the same external stimulator electronics 34 can be used in the embodiments of FIG. 1 and FIG. 2. As shown in FIG. 2, the external stimulator electronics 34 preferably are driven in direct electrical stimulation mode, i.e., current is supplied to the electrodes 40 and 42 directly through the cable 32.

Figure 3:
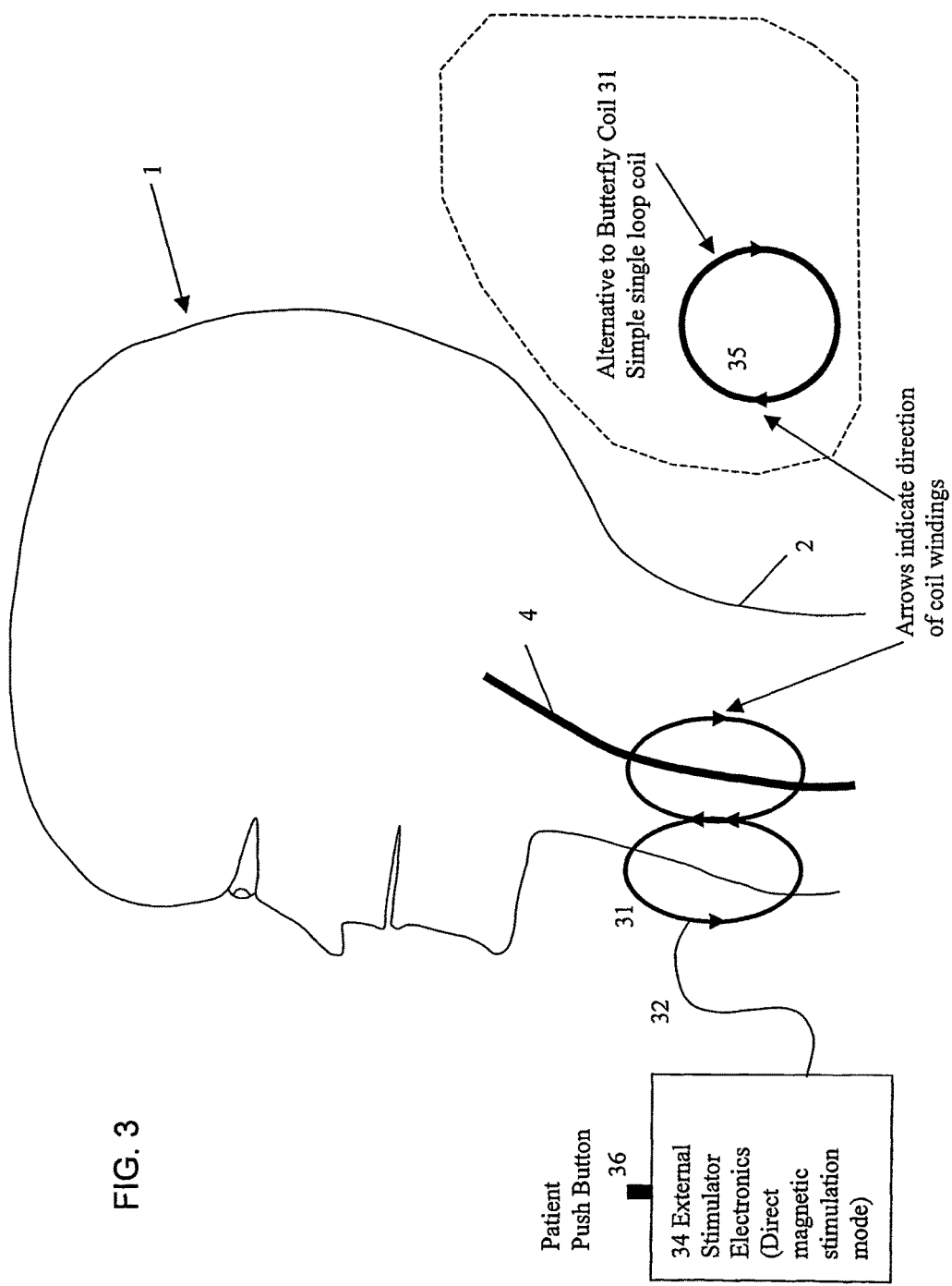
FIG. 3 is a schematic view of a further alternate system and method for driving the external stimulator electronics in a direct magnetic stimulation mode.

FIG. 3 depicts an alternate method of driving current from the external stimulator electronics and power supply 34. In FIG. 3, the current is driven by direct magnetic stimulation, in which the inductive loop transmitter 30 of FIG. 1 has been replaced by a magnetic stimulator coil 31. FIG. 3 depicts the magnetic stimulator coil 31 as a butterfly coil, where the butterfly coil 31 can provide shallow direct magnetic stimulation. Alternatively, other coil configurations can be used, such as a simple single loop coil 35 which can provide deeper magnetic stimulation. In the embodiment of FIG. 3, the external stimulator electronics and power supply 34 are driven to produce high current waveforms needed for magnetic stimulation. The magnetic stimulator coil 31 is placed over the neck in the vicinity of the vagus nerve 4, thereby directly stimulating the vagus nerve. In the embodiment of FIG. 3, no electrodes or other implanted components are required.

In other embodiments of the present invention, electrodes can be placed on the skin of the abdomen, or under the skin of the abdomen, in the vicinity of the vagus nerve. For example, electrodes can be placed on or near the stomach and/or esophagus.

FIGS. 4A and 4B depict the methods illustrated in FIGS. 1 and 2, respectively, whereby one or more electrodes are arranged in the vicinity of the vagus nerve on or near the esophagus and/or stomach. Electrodes also could be arranged on or near the duodenum or intestines.

As shown in FIG. 4A, one or more electrodes 10 and 12 are implanted under the skin of the patient on or near the esophagus 50 and/or the stomach 52, in the vicinity of the vagus nerve (not shown). One or more leads or wires 14 connect each electrode to an optional internal stimulator electronics package 22. The internal stimulator electronics 22 receive power and control from inductive link coil 26 via one or more wires or leads 24, as described above with reference to FIG. 1. According to the embodiment depicted in FIG. 4A, it is possible to stimulate the vagus nerve by implanting electrodes on or near the esophagus and/or stomach, and otherwise operating the system in the manner described above.

FIG. 4B depicts one or more electrodes 40 and 42 placed on the body surface 51 of the chest or abdomen, so as to be above the esophagus, stomach, duodenum, or intestines. As shown in FIG. 4B, external stimulator electronics 34 are driven in direct electrical stimulation mode, in the manner described above with reference to FIG. 2. Therefore, according to the embodiment of FIG. 4B, it is possible to stimulate the vagus nerve by placing electrodes on or under the skin covering the chest or abdomen, so as to stimulate the esophagus, stomach, duodenum, or intestines, or their nerves.

FIGS. 5A and 5B are block diagrams illustrating the internal stimulator electronics 22 and the external stimulator electronics 34, respectively.

The internal stimulator electronics 22 of FIG. 5A receive power and control from the inductive link coil 26 (see FIG. 1) via one or more leads 24. A power signal separator 60 preferably converts AC power received from the inductive link coil 26 into DC power, which is supplied to a rectifier and capacitor 62 for controlling circuits of the internal stimulator electronics 22. Control signals from the power signal separator 60 are transmitted to a control processor 64, the control signals being used to drive a stimulus pulse generator 66, which provides stimulating current and regulates the pulses delivered to the electrodes 10 and 12 over the leads 14. The aforementioned components of the internal stimulator electronics 22 are depicted for illustrative purposes only, and could be modified or substituted as needed.

FIG. 5B depicts the external stimulator electronics and power supply 34. A power oscillator 70 drives the inductive loop coil 30 (see FIG. 1) via one or more leads 32 preferably with an alternating current. A control processor 72 controls the power oscillator 70 and is operably connected to the patient push button 36. In addition, the control processor 72, under the direction of a mode selection program 76, can change the waveforms produced by the power oscillator 54 to produce high current waveforms for direct magnetic stimulation as needed (see FIG. 3). A conventional power supply 78 provides all power needed by the system, and is connected to the control processor 72 and the power oscillator 70.

As discussed above, methods and systems of the invention are employed to treat a patient, such as a mammal particularly a human that is suffering from or susceptible to nausea and/or vomiting. For instance, methods of the invention are particularly useful for treating a pregnant female, including a human female in her first, second or third trimester of pregnancy. Also, the methods of the invention are useful for treating nausea and/or vomiting as the result of chemotherapy treatments for connective tissue diseases, or inflammatory or autoimmune disorders of the peripheral or central nervous system, or patients suffering from severe motion sickness. Preferably, a subject (such as a human) is identified and/or selected that is susceptible or suffering from prolonged periods (e.g. greater than 12, 24, 48, or 96 hours) of experiencing vomiting and/or sensations of nausea, and the identified and/or selected subject is treated in accordance with the invention, e.g. applying one or more electrodes on (includes proximate to) or under the skin of the identified and/or selected subject; connecting the electrodes to an external current source; and passing current from the external current source to the electrodes, thereby stimulating the vagus nerve to reduce nausea and vomiting of the subject. This invention may also be used to treat the selected patient by passing a current through an external coil that produces magnetic stimulation, thereby activating the vagus nerve. The treated subject may be free or at least asymptomatic of other diseases and/or disorders such as epilepsy and seizures, psychiatric disorders, heart disorders, and pain not associated with nausea and/or vomiting.

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications and other references cited herein are hereby expressly incorporated herein in their entireties by reference.

What is claimed is:

1. A method for treating nausea and/or vomiting caused by pregnancy, motion sickness, or chemotherapy, comprising the steps of:
   implanting two or more electrodes below a sternocleidomastoid muscle proximate to a left vagus nerve in the neck of a patient in need of treatment of nausea and/or vomiting caused by pregnancy, motion sickness, or chemotherapy;
   executing a mode selection program that predefines a plurality of selectable stimulation modes for stimulating the left vagus nerve using an external current source, wherein the plurality of selectable stimulation modes include:
   (i) an inductive stimulation mode in which electrical current is inductively applied to the two or more implanted electrodes,
   (ii) a direct electrical stimulation mode in which electrical current is directly applied to electrodes placed proximate to the left vagus nerve on a skin surface of the neck of the patient, and
   (iii) a direct magnetic stimulation mode in which electrical current is applied to a magnetic stimulator coil configured to produce magnetic stimulation and positioned proximate to the left vagus nerve over the neck of the patient;
   receiving a selection of the inductive stimulation mode via the mode selection program;
   in response to the selection of the inductive stimulation mode, causing, by the mode selection program, a control processor of the external current source to change a current waveform produced by a power oscillator of the external current source in accordance with the inductive stimulation mode, wherein each of the plurality of selectable stimulation modes corresponds to a specific current waveform; and
   controlling, by the control processor, the external current source to apply electrical current with the current waveform produced by the power oscillator to the two or more implanted electrodes, thereby stimulating the left vagus nerve and treating the nausea and/or vomiting of the patient caused by pregnancy, motion sickness, or chemotherapy.

2. The method of claim 1, wherein the current is passed to the two or more electrodes by magnetic induction.

3. The method of claim 1, wherein the two or more electrodes are connected to an inductive pickup loop implanted under the skin, and optionally to internal electronics.

4. The method of claim 3, wherein an inductive loop transmitter is connected to the external current source.

5. The method of claim 4, wherein the inductive loop transmitter and the inductive pickup loop form a magnetic inductive link.

6. A method for treating nausea and vomiting caused by pregnancy, motion sickness, or chemotherapy, comprising the steps of:
   placing two or more electrodes on the skin of the neck of a patient, wherein the one or more electrodes are positioned over a sternocleidomastoid muscle;
   connecting the electrodes to an external current source;
   executing a mode selection program that predefines a plurality of selectable stimulation modes for stimulating the left vagus nerve in the neck of the patient using the external current source, wherein the plurality of selectable stimulation modes include:
   (i) an inductive stimulation mode in which electrical current is inductively applied to electrodes implanted below the sternocleidomastoid muscle proximate to the left vagus nerve in the neck of the patient,
   (ii) a direct electrical stimulation mode in which electrical current is directly applied to the electrodes placed on the skin of the neck of the patient, and (iii) a direct magnetic stimulation mode in which electrical current is applied to a magnetic stimulator coil configured to produce magnetic stimulation and positioned proximate to the left vagus nerve over the neck of the patient;

receiving a selection of the direct electrical stimulation mode via the mode selection program;

in response to the selection of the direct electrical stimulation mode, causing, by the mode selection program, a control processor of the external current source to change a current waveform produced by a power oscillator of the external current source in accordance with the direct electrical stimulation mode, wherein each of the plurality of selectable stimulation modes corresponds to a specific current waveform; and controlling, by the control processor, the external current source to apply electrical current with the current waveform produced by the power oscillator to the electrodes, thereby stimulating the left vagus nerve to reduce nausea and vomiting caused by pregnancy, motion sickness, or chemotherapy.

7. The method of claim 6, wherein the two or more electrodes are positioned over a medial region of the sternocleidomastoid muscle.

8. A method for treating nausea and vomiting caused by pregnancy, motion sickness, or chemotherapy, comprising the steps of:

placing a magnetic stimulation coil on the skin of the neck of a patient, wherein the magnetic stimulation coil is configured to produce magnetic stimulation and positioned over a sternocleidomastoid muscle;

connecting the magnetic stimulation coil to an external current source;

executing a mode selection program that predefines a plurality of selectable stimulation modes for stimulating the left vagus nerve in the neck of the patient using the external current source, wherein the plurality of selectable stimulation modes include:

(i) an inductive stimulation mode in which electrical current is inductively applied to electrodes implanted below the sternocleidomastoid muscle proximate to the left vagus nerve in the neck of the patient, (ii) a direct electrical stimulation mode in which electrical current is directly applied to electrodes placed on the skin of the neck of the patient, and (iii) a direct magnetic stimulation mode in which electrical current is applied to the magnetic stimulator coil;

receiving a selection of the direct magnetic stimulation mode via the mode selection program;

in response to the selection of the direct magnetic stimulation mode, causing, by the mode selection program, a control processor of the external current source to change a current waveform produced by a power oscillator of the external current source in accordance with the direct magnetic stimulation mode, wherein each of the plurality of selectable stimulation modes corresponds to a specific current waveform; and controlling, by the control processor, the external current source to apply electrical current with the current waveform produced by the power oscillator to the magnetic stimulation coil, thereby stimulating the left vagus nerve to reduce nausea and vomiting caused by pregnancy, motion sickness, or chemotherapy.

9. A method for treating nausea and vomiting caused by pregnancy, motion sickness, or chemotherapy, comprising:

implanting two or more electrodes connected to an inductive pickup loop below a sternocleidomastoid muscle proximate to a left vagus nerve in the neck of a patient in need of treatment of nausea and/or vomiting caused by pregnancy, motion sickness, or chemotherapy;

executing a mode selection program that predefines a plurality of selectable stimulation modes for stimulating the left vagus nerve using an external current source connected to an inductive loop transmitter externally positioned on the neck of the patient proximate to the two or more implanted electrodes, wherein the plurality of selectable stimulation modes include:

(i) an inductive stimulation mode in which electrical current is inductively applied to the two or more implanted electrodes via the inductive pickup loop, (ii) a direct electrical stimulation mode in which electrical current is directly applied to electrodes placed proximate to the left vagus nerve on a skin surface of the neck of the patient, and (iii) a direct magnetic stimulation mode in which electrical current is applied to a magnetic stimulator coil configured to produce magnetic stimulation and positioned proximate to the left vagus nerve over the neck of the patient;

receiving a selection of the inductive stimulation mode via the mode selection program;

in response to the selection of the inductive stimulation mode, causing, by the mode selection program, a control processor of the external current source to change a current waveform produced by a power oscillator of the external current source in accordance with the inductive stimulation mode, wherein each of the plurality of selectable stimulation modes corresponds to a specific current waveform; and controlling, by the control processor, the external current source to apply electrical current with the current waveform produced by the power oscillator to the inductive loop transmitter, thereby stimulating the left vagus nerve and treating the nausea and/or vomiting of the patient caused by pregnancy, motion sickness, or chemotherapy.

10. The method of claim 9, wherein the stimulation is actuated manually.

11. The method of claim 9, wherein the stimulation is actuated automatically.

12. The method of claim 9, wherein the stimulation is turned on and off automatically at designated times.

* * * * *